(12) United States Patent
Chern Lin et al.

(10) Patent No.: US 6,726,787 B2
(45) Date of Patent: *Apr. 27, 2004

(54) PROCESS FOR MAKING A WORK PIECE HAVING A MAJOR PHASE OF α FROM A TITANIUM ALLOY

(75) Inventors: Jiin-Huey Chern Lin, 911 Tower Rd., Winnetka, IL (US) 60093; Chien-Ping Ju, 16 Pinewood Dr., Carbondale, IL (US) 62901; Chih-Min Lee, Kaohsiung (TW)

(73) Assignees: Jiin-Huey Chern Lin, Winnetka, IL (US); Chien-Ping Ju, Carbondale, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/327,992

(22) Filed: Dec. 26, 2002

(65) Prior Publication Data

US 2003/0094222 A1 May 22, 2003

Related U.S. Application Data

(63) Continuation-in-part of application No. 10/157,121, filed on May 30, 2002, which is a continuation-in-part of application No. 10/134,524, filed on Apr. 30, 2002, which is a continuation-in-part of application No. 09/266,204, filed on Jan. 7, 1999, now Pat. No. 6,409,852.

(51) Int. Cl.$^7$ .................................................. C22F 1/18

(52) U.S. Cl. ...................... 148/669; 148/421; 420/421; 420/417

(58) Field of Search ................................ 148/669, 421; 420/421, 417

(56) References Cited

U.S. PATENT DOCUMENTS 5,205,984 A * 4/1993 Rowe .......................... 420/420
5,906,692 A * 5/1999 Bhowal et al. ............. 148/671

* cited by examiner

Primary Examiner—Andrew L. Oltmans
(74) Attorney, Agent, or Firm—Bacon & Thomas, PLLC

(57) ABSTRACT

Quenching a work piece made of a titanium alloy having a temperature higher than 800° C. to a temperature lower than 500° C. at a cooling rate greater than 10° C./second between 800° C. and 500° C. is used to render the cooled work piece containing α" phase as a major phase. The titanium alloy composition contains at least one isomorphous beta stabilizing element selected from Mo, Nb, Ta and W; and the balance Ti, wherein said composition has a Mo equivalent value from about 6 to about 9. The work piece is preferably a medical device.

12 Claims, No Drawings

PROCESS FOR MAKING A WORK PIECE HAVING A MAJOR PHASE OF α FROM A TITANIUM ALLOY

CROSS-REFERENCE TO RELATED APPLICATION

The present application is a continuation-in-part application of U.S. patent application Ser. No. 10/157,121, filed May 30, 2002, which is a continuation-in-part application of U.S. patent application Ser. No. 10/134,524, filed Apr. 30, 2002, which is a continuation-in-part application of U.S. patent application Ser. No. 09/226,204, filed Jan. 7, 1999, now U.S. Pat. No. 6,409,852B1. The above-listed applications are commonly assigned with the present invention and the entire contents of which are incorporated herein by reference.

FIELD OF THE INVENTION

The present invention is related to a process for making a work piece having a major phase of α" from a titanium alloy, and in particular a process for making a biocompatible low modulus high strength titanium-based medical device having a major phase of α".

BACKGROUND OF THE INVENTION

Titanium and titanium alloys have been popularly used in many medical applications due to their light weight, excellent mechanical performance and corrosion resistance. The relatively low strength commercially pure titanium (c.p. Ti) is currently used as dental implant, crown and bridge, as well as denture framework. With a much higher strength than c.p. Ti, Ti-6Al-4V alloy has been widely used in a variety of stress-bearing orthopedic applications, such as hip prosthesis and artificial knee joint. Moreover, the lower elastic modulus allows the titanium alloy to more closely approximate the stiffness of bone for use in orthopedic devices compared to alternative stainless steel and cobalt-chrome alloys in orthopedic implants. Thus, devices formed from the titanium alloy produce less bone stress shielding and consequently interfere less with bone viability.

Various attempts at providing low modulus, high strength titanium alloys for making medical implants with less stress shielding have been proffered by the prior art. There is still a great interest in finding a lower modulus and higher strength titanium alloys. In addition, studies have reported that the release of Al and V ions from the medical implants might cause some long-term health problems, for example the low wear resistance of Ti-6Al-4V alloy could accelerate the release of such harmful ions.

SUMMARY OF THE INVENTION

A primary objective of the present invention is to provide a process for making a work piece, and in particular a biocompatible low modulus high strength medical device, from a titanium alloy free from potential harmful components.

Another objective of the present invention is to provide a process for making a work piece, and in particular a biocompatible low modulus high strength medical device, from a titanium alloy having a major phase of α".

In order to achieve the aforesaid objectives a process for making a work piece having an α" phase as a major phase from a titanium alloy according to the present invention comprises the following steps:

a) preparing a titanium alloy composition comprising at least one isomorphous beta stabilizing element selected from the group consisting of Mo, Nb, Ta and W; and the balance Ti, wherein said composition has a Mo equivalent value from about 6 to about 9;

b) fast cooling said composition having a temperature higher than 800° C. to a temperature lower than 500° C. at a cooling rate greater than 10° C./second between 800–500° C., so that the resulting cooled composition contains an α" phase as a major phase.

Preferably, said titanium alloy composition in step a) is substantially free from an eutectoid beta stabilizing element selected from the group consisting of Fe, Mn, Cr, Co, and Ni.

Preferably, said titanium alloy composition in step a) is substantially free from Al.

Preferably, said titanium alloy composition in step a) is substantially free from V.

Preferably, said titanium alloy composition in step a) consists essentially of at least one isomorphous beta stabilizing element selected from the group consisting of Mo, Nb, Ta and W; and the balance Ti.

Preferably, said cooling rate is greater than 20° C./sec.

Preferably, said fast cooling in step b) comprises water quenching.

Preferably, said composition has a temperature of 800–1200° C. before said fast cooling in step b).

Preferably, said preparing in step a) of the process of the present invention comprises casting said titanium alloy composition to form a work piece having a temperature higher than 800° C., and said fast cooling in step b) comprises fast cooling said work piece having a temperature higher than 800° C.

Preferably, said preparing in step a) of the process of the present invention comprises metal working said titanium alloy composition to form a work piece, and heating the resulting work piece to a temperature higher than 800° C., and said fast cooling in step b) comprises fast cooling said work piece having a temperature higher than 800° C.

Preferably, said titanium alloy composition in step a) further comprises one or more incidental impurities selected from the group consisting of carbon, oxygen and nitrogen, wherein a total amount of said one or more incidental impurities is less than 1 wt %.

Preferably, said work piece having a major phase of α" is a medical device.

DETAILED DESCRIPTION OF THE PREFERRED EMBODIMENTS

The present invention provides a process for making a biocompatible low modulus high strength medical device from a titanium alloy, which comprises preparing a titanium alloy having a composition consisting essentially of at least one isomorphous beta stabilizing element selected from the group consisting of Mo, Nb, Ta and W; and the balance Ti, wherein said composition has a Mo equivalent value from about 6 to about 9; casting or metal working the titanium alloy to form a work piece; and quenching the work piece which is the resulting hot cast having a temperature higher than 800° C. at a cooling rate greater than 10° C. per second, or heating the work piece resulted from said metal working to a temperature higher than 800° C. and quenching the work piece having a temperature higher than 800° C. at a cooling rate greater than 10° C. per second, so that the cooled work piece contains an α" phase as a major phase, and can be used as a medical device which is biocompatible, and has a low modulus and high strength.

In the present invention, said Mo equivalent value, [Mo]eq, can be represented by the following equation:

[Mo]eq=[Mo]+0.28[Nb]+0.22[Ta]+0.44[W]

wherein [Mo]wt %, [Nb]wt %, [Ta]wt % and [W]wt % are percentages of Mo, Nb, Ta and W, respectively, based on the weight of the composition.

The casting and the metal working suitable for use in the process of the present invention are not limited, and can be any known techniques in the art.

A typical quenching method used in the process of the present application is water quenching; however, any methods known in the art which have a cooling rate greater than 10° C., preferably 20° C., per second, can also be used.

The medical device prepared by the process of the present invention can be an orthopedic implant, a dental implant, a dental crown, a dental bridge or a denture framework.

Some of the preferred embodiments according to the present invention will be described in the following examples, that are intended as illustrative only since numerous modifications and variations therein will be apparent to those skilled in the art.

EXAMPLE 1

Ti-7.5Mo alloy (7.5 wt % Mo) was prepared from a commercially pure titanium (c.p. Ti) bar, and molybdenum of 99.95% purity using a commercial arc-melting vacuum-pressure type casting system (Castmatic, Iwatani Corp., Japan). The melting chamber was first evacuated and purged with argon. An argon pressure of 1.5 kgf/cm$^2$ was maintained during melting. Appropriate amounts of the c.p. Ti bar and molybdenum wire (92.5 wt % Ti-7.5 wt % Mo) were melted in a U-shaped copper hearth with a tungsten electrode. The ingot was re-melted three times to improve chemical homogeneity.

A specimen having an outer diameter of 7 mm and a length of 29 mm was prepared from the Ti-7.5Mo alloy, at one end of which was further provided with a hole having a diameter of 3.5 mm and a depth of 12 mm for mounting a K-type thermalcouple therein. A titanium in the form of a sponge was received in a quartz tube and fixed at a bottom thereof by a quartz cap, and the specimen equipped with the thermalcouple was inserted into the quartz tube and hermetically mounted inside the quartz tube with one end of the thermalcouple being connected to a temperature recorder (ss. 250 Recorder, Sekonic, Japan). The quartz tube at the sealed end was further equipped with a vacuum pump, and a vacuum meter. The quartz tube was vacuumed for five minutes, and placed in an air furnace (s19, Nabertherm®, Germany) preheated at 1000° C. for 30 minutes. The quartz tube was removed from the air furnace, and the specimen together with the thermalcouple was subjected to water quenching. The average cooling rates recorded was 118° C./sec.

X-ray diffraction (XRD) for phase analysis of the cooled specimen was conducted using a Rigaku diffractometer (Rigaku D-max IIIV, Rigaku Co., Tokyo, Japan) operated at 30 kV and 20 mA. A Ni-filtered CuK$_\alpha$ radiation was used for this study. A silicon standard was used for calibration of diffraction angles. Scanning speed of 3°/min was used. The phase was identified by matching each characteristic peak in the diffraction pattern with the JCPDS files.

Three-point bending tests were performed using a desktop mechanical tester (Shimadzu AGS-500D, Tokyo, Japan) operated at 0.5 mm/sec. Reduced size (36×5×1 mm) specimens were cut from the castings and polished using sand paper to a #1000 level. The bending strengths were determined using the equation, $\sigma=3PL/2bh^2$ where $\sigma$ is bending strength (MPa); P is load (Kg); L is span length (mm); b is specimen width (mm) and h is specimen thickness (mm). The modulus of elasticity in bending was calculated from the load increment and the corresponding deflection increment between the two points on a straight line as far apart as possible using the equation, $E=L^3\Delta P/4bh^3\Delta\delta$ where E is modulus of elasticity in bending (Pa); $\Delta P$ is load increment as measured from preload (N); and $\Delta\delta$ is deflection increment at midspan as measured from preload. The average bending strength and modulus of elasticity in bending were taken from at least six tests under each condition.

Various Ti alloys were also prepared and tested according to the aforesaid procedures in Example 1. Table 1 lists the weight percentages of the starting metals in the preparation of the Ti alloys of the present invention and the test results thereof, wherein data of the c.p. Ti (Grade II) and Ti-6Al-4V alloy are also included for comparison.

TABLE 1

| Alloy system | [Mo]eq | Phase | Bending strength (MPa) | Bending modulus (GPa) | Strength/modulus ratio (× 10$^3$) |
|---|---|---|---|---|---|
| Ti-7.5Mo | 7.5 | α" | 1395 | 55 | 25.4 |
| Ti-17.5Nb | 4.9 | α" | 1472 | 59.4 | 24.8 |
| Ti-20Nb | 5.6 | α" | 1466 | 60.4 | 24.3 |
| Ti-22.5Nb | 6.2 | α" | 1509 | 68.5 | 22.0 |
| Ti-25Nb | 6.9 | α" | 1656 | 77.1 | 21.5 |
| Ti-5Mo-12.5Ta | 7.5 | α" | 1525 | 69.2 | 22.0 |
| Ti-5Mo-15Ta | 8.0 | α" | 1497 | 66.7 | 22.4 |
| Ti-6Mo-5Nb | 7.4 | α" | 1477 | 69.1 | 21.3 |
| Ti-6Mo-7Ta | 7.54 | α" | 1489 | 70.4 | 21.1 |
| Ti-6Mo-3W | 7.32 | α" | 1401 | 64.6 | 21.6 |
| Ti-7.5Mo-1Nb | 7.78 | α" | 1680 | 64 | 26.3 |
| Ti-7.5Mo-2.5Ta | 8.0 | α" | 1649 | 66.9 | 24.6 |
| Ti-7.5Mo-5Ta | 8.5 | α" | 1724 | 71.2 | 24.2 |
| Ti-7.5Mo-7.5Ta | 9.0 | α" | 1759 | 73 | 24.1 |
| Tu-6Mo-3Nb-3Ta | 7.5 | α" | 1436 | 67.6 | 21.2 |
| Ti-6Mo-3Nb-1.5W | 7.5 | α" | 1398 | 66.9 | 20.8 |
| Ti-6Mo-3Ta-1.5W | 7.32 | α" | 1451 | 65.2 | 22.2 |
| c.p. Ti (Grade II) | 0 | α' | 884 | 92 | 9.6 |
| Ti-6Al-4V | 2.7 | α + β | 1857 | 105 | 17.7 |

It can be seen from Table 1 that the Ti alloys prepared according to the process of the present invention all have an α" phase, and have a high bending strength and a low modulus (high strength/modulus ratios) compared to the prior art Ti-6Al-4V alloy.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A process for making a work piece having an α" phase as a major phase from a titanium alloy composition comprising the following steps:
   a) preparing a titanium alloy composition comprising at least one isomorphous beta stabilizing element selected from the group consisting of Mo, Nb, Ta and W; and the balance Ti, wherein said composition has a Mo equivalent value from about 6 to about 9;

b) fast cooling said composition having a temperature higher than 800° C. to a temperature lower than 500° C. at a cooling rate greater than 10° C./second between 800–500° C., so that the resulting cooled composition contains an α" phase as a major phase.

2. The process according to claim 1, wherein said titanium alloy composition in step a) is substantially free from an eutectoid beta stabilizing element selected from the group consisting of Fe, Mn, Cr, Co, and Ni.

3. The process according to claim 1, wherein said titanium alloy composition in step a) is substantially free from Al.

4. The process according to claim 1, wherein said titanium alloy composition in step a) is substantially free from V.

5. The process according to claim 1, wherein said titanium alloy composition in step a) consists essentially of at least one isomorphous beta stabilizing element selected from the group consisting of Mo, Nb, Ta and W; and the balance Ti.

6. The process according to claim 1, wherein said cooling rate in step b) is greater than 20° C./sec.

7. The process according to claim 6, wherein said fast cooling comprises water quenching.

8. The process according to claim 1, wherein said composition has a temperature of 800–1200° C. before said fast coolig in step b).

9. The process according to claim 1, wherein said preparing in step a) comprises casting said titanium alloy composition to form a work piece having a temperature higher than 800° C., and said fast cooling in step b) comprises fast cooling said work piece having a temperature higher than 800° C.

10. The process according to claim 1, wherein said preparing in step a) comprises metal working said titanium alloy composition to form a work piece, and heating the resulting work piece to a temperature higher than 800° C., and said fast cooling in step b) comprises fast cooling said work piece having a temperature higher than 800° C.

11. The process according to claim 1, wherein said titanium alloy composition in step a) further comprises one or more incidental impurities selected from the group consisting of carbon, oxygen and nitrogen, wherein a total amount of said one or more incidental impurities is less than 1 wt %.

12. The process according to claim 1, wherein said work piece having a major phase of α" is a medical device.

* * * * *